United States Patent [19]

Grzywa et al.

[11] Patent Number: 4,906,789

[45] Date of Patent: Mar. 6, 1990

[54] METHODS FOR BISPHENOL A PRODUCTION

[75] Inventors: Edward Grzywa, Warsaw; Maciej Kiedik, Kędzierzyn-Koźle; Jó Kolt, Zabrze; Adam Mazur, Kędzierzyn-Koźle; Jerzy Marszycki, Kędzierzyn-Koźle; Eugeniusz Zając, Kędzierzyn-Koźle; Anna Rzodeczko, Kędzierzyn-Koźle; Jerzy Czyż, Kędzierzyn-Koźle; Kazimierz Terelak, Kędzierzyn-Koźle; Zbigniew Swiderski, Kędzierzyn-Koźle; Teodor Bek, Kędzierzyn-Koźle, all of Poland

[73] Assignees: Instytut Ciezkiej Syntezy Organicznej "Blachownia"; Zaklady Chemiczne "Blachownia", both of Kędzierzyn-Koźle, Poland

[21] Appl. No.: 250,393

[22] Filed: Sep. 28, 1988

[30] Foreign Application Priority Data

Oct. 7, 1987 [PL] Poland ................................ 268149

[51] Int. Cl.$^4$ ...................... C07C 39/16; C07C 37/00; C07C 37/11
[52] U.S. Cl. .................................................... 568/727
[58] Field of Search ................................ 568/727, 728

[56] References Cited

U.S. PATENT DOCUMENTS

| | | | |
|---|---|---|---|
| 3,049,569 | 8/1962 | Apel et al. | 568/728 |
| 3,221,061 | 11/1965 | Grover et al. | 568/728 |
| 4,301,305 | 11/1981 | Kiedik et al. | 568/728 |
| 4,319,053 | 3/1982 | Heuser et al. | 568/728 |
| 4,391,997 | 7/1983 | Mendiratta | 568/727 |

*Primary Examiner*—Werren B. Lone
*Attorney, Agent, or Firm*—Bauer & Schaffer

[57] ABSTRACT

A process for the production of bisphenol A from phenol and acetone, comprises introducing a substantially anhydrous reaction mixture of phenol, acetone, and recycled solution of bisphenol A and reaction by-products in phenol into a reaction zone containing a cation-exchange resin catalyst, such catalyst being a mixture of resin having a macroporous structure and resin having a microporous structure in a ratio of 0.05:1 to 0.5:1 by weight, the mol ratio of phenol to acetone being 5:1 to 30:1, and the concentration of bisphenol A being 12 to 20% by weight. The temperature of the reaction zone is maintained between 60 degrees and 95 degrees C. The resulting reacted reaction mixture is withdrawn from the reaction zone, the concentration of bisphenol A being 21 to 35% by weight and the amount of reaction by-products being 12 to 24% by weight. Such withdrawn reaction mixture is treated to recover bisphenol A product and to provide the recycled solution of bisphenol A and reaction by-products in phenol.

7 Claims, No Drawings

METHODS FOR BISPHENOL A PRODUCTION

BACKGROUND OF THE INVENTION

This invention relates to a method for bisphenol A production by condensation of phenol with acetone in the presence of an acid ion exchangable resin catalyst.

There are known many methods for obtaining bisphenol A by the use of an acid ion exchangable resin catalyst.

In the method known from Polish Patent 96346, condensation of phenol with acetone is conducted with multiple circulation of the reaction mixture through a cation-exchange resin bed of sulfonated copolymer of styrene and divinylbenzene in three stages, with dosing of acetone to the reaction mixture which contains also recycled by-products of the reaction. This method can be performed periodically or continuously.

Further development of the above-mentioned method is described in U.S. Pat. No. 4,301,305 according to which, the process of condensation of phenol with acetone is conducted continuously in three stages in two reactors having stationary cation-exchange resin beds. The catalyst bed in each reactor is 15–20 m high and is divided into a lower zone and an upper zone. The reaction mixture is circulated through each catalyst bed in various stages of the process at various linear velocities.

The first stage of the reaction is carried out in the first reactor in sequence in the lower zone and then in the upper zone of the catalyst bed at a temperature of 60–85 degress C. The second stage of the process is carried out at a temperature of 65–90 degrees C in the lower zone of the catalyst bed of the second reactor; and the third stage of the process is carried out in the upper zone of the second reactor at a temperature of 70–95 degrees C.

The linear velocity of the reaction mixture flow through the lower zone of the catalyst bed of each reactor, does not exceed 10 m/h; and the velocity of the reaction mixture flow through the upper zone of the catalyst bed in each reactor does not exceed 4 m/h. The mixture charged to the reactors contains 11 percent by weight of bisphenol A and 10.5 percent by weight of reaction by-products. The method according to Polish Patent 96346 and U.S. Pat. No. 4,301,305 permits the reaction of phenol with acetone to be carried out with relatively high selectivity.

The method of bisphenol A production, according to U.S. Pat. No. 3,049,569 proceeds in several stages. It comprises condensation of acetone with phenol, the latter being in stoichiometric excess, in an anhydrous medium at a temperature from about 30 degrees C to about 125 degrees C in a bed of an insoluble cation-exchangable resin. A part of the acetone and the phenol in the reaction zone remains in the liquid phase between the start and the finish of the reaction. As a result, there is formed an incompletely reacted post-reaction mixture containing bisphenol A, an adduct of bisphenol A and phenol, unreacted acetone, unreacted phenol, by-products of the reaction and water. Incompletely reacted post-reaction mixture is first divided into an upper stream containing acetone, water and phenol and a lower stream containing bisphenol A, the adduct of bisphenol A and phenol, and the by-products of the reaction. The upper stream is dehydrated and substantially anhydrous phenol and acetone are recycled to the reaction zone. From the lower stream there is separated the adduct of bisphenol A and phenol; and the remaining part of the lower stream is recycled to the reaction zone. Next, bisphenol A is separated from its adduct with phenol, and the phenol is recycled to the reaction zone. The characteristic features of this method are recycling of the by-products of the reaction to the reaction zone in order to reduce their formation and the use of single flow of the reaction mixture through the cation-exchange resin bed with a short residence time in the reaction zone.

Under these conditions 50 percent of the acetone is reacted and the reaction is carried out with a concentration of bisphenol A between 4–6 percent by weight in the charge mixture to the reaction zone and 12–14 percent by weight in the post-reaction mixture.

Recycling of the by-products of the reaction to the reaction zone was expected to influence their level at about 8 percent by weight in the reaction mixture, which would enable high selectivity of the reaction of phenol with acetone.

However, in industrial practice it appears that, in spite of considerable advantages such as the high efficiency of the reaction based on the catalyst volume and the simplicity of the technological process, the method of bisphenol A production according to U.S. Pat. No. 3,049,569 did not provide appropriately high selectivity of the reaction of phenol with acetone and the required purity of the desired product. It also appeared that it was impossible to achieve the assumed state of equilibrium for some by-products of the reaction, for instance, for the o-p-bisphenol A isomer and that the process could not be performed for a long period of time without loss of a considerably quantity of by-products of the reaction.

Proof for the above-mentioned fact is the method disclosed in U.S. Pat. No. 3,221,061 which method comprises exposing the by-products of the reaction to a cation-exchange resin for their partial isomerization and rearrangement, with resulting reduction of the by-products of the reaction. However, this procedure did not solve the problem completely since additional decomposition of some by-products of the reaction in the presence of an alkaline catalyst is required for improvement of the general selectivity of the process.

In spite of so many improvements of the method of bisphenol A production known from U.S. Pat. No. 3,049,569, it is still subject to relatively low selectivity with simultaneous high energy consumption resulting from low concentration of bisphenol A in the post-reaction mixture and the necessity to handle a large quantity of diluted phenol solution.

An improvement of the above-discussed process is described in U.S. Pat. No. 4,308,405 and comprises recycling a part of the stream obtained by drying of the post-reaction mixture to the reaction zone in order to reduce the quantity of phenol to be removed by evaporation from the post-reaction mixture before bisphenol A is separated from it.

A further attempt to improve the process selectivity is described in U.S. Pat. No. 4,391,997 and comprises increasing the temperature of the reaction mixture as its passes through the reaction zone in order to reduce formation of by-products of the reaction and to improve the color of the reaction mixture.

This method, which is similar to the above-mentioned methods known from Polish Patent 96346 and U.S. Pat. No. 4,301,305, basically differs from them in that it deals with a single flow of the reaction mixture through the cation-exchange resin bed.

The above-mentioned facts show that the problem of selectivity of the reaction of acetone with phenol to form bisphenol A in the presence of a cation-exchange resin catalyst has not been solved to a satisfactory extend and that the consumption of phenol and acetone still differs considerably from the stoichiometric data.

SUMMARY OF THE INVENTION

The present invention provides an improved method for the production of bisphenol A by the reaction of phenol with acetone in the presence of a cation-exchange resin catalyst utilizing substantially anhydrous post-crystallization liquors comprising a solution of bisphenol A and by-products of the reaction in phenol. The reaction of phenol with acetone is carried out with 12 to 20 percent by weight initial concentration of bisphenol A in the reaction mixture, desirably 15 to 18 percent by weight, to a final concentration of bisphenol A in the reacted reaction mixture 21 to 35 percent by weight, desirably 22 to 28 percent by weight, and with the reaction by-products content in the reaction mixture being 12 to 24 percent by weight, desirably 16 to 20 percent by weight. The process is conducted at a temperature of 60 to 95 degrees C with the mole ratio of phenol to acetone being 5:1 to 30:1. The reaction mixture charged to the reaction zone includes recycled solution of bisphenol A and reaction by-products in phenol preferably with a part of the reaction mixture taken from the reaction system. The catalyst is a mixture of a cation-exchange resin having a macroporous structure and a cation-exchange resin having a microporous structure in a weight ratio of 0.05:1 to 0.5:1. The content of bisphenol A isomers in the reaction by-products in the charged reaction mixture is less than ¼.

During tests on this process, it was found that considerably higher selectivity of the reaction of phenol with acetone, to form bisphenol A in relation to the known processes is obtained. This achievement results from conducting the process within the specified ranges of the component concentrations in the reaction mixture, which are higher than the ones used previously with the reaction by-products concentration being simultaneously higher than hitherto.

DESCRIPTION OF THE PREFERRED EMBODIMENTS

It is desirable to carry out the reaction with flow of the reaction mixture through a loose cation-exchange resin bed, preferably by flow of the reaction mixture in the upward direction.

It is also desirable to keep a low concentration of ortho-para and ortho-ortho isomers among the by-products of the reaction recycled to the reaction zone and to utilize as a catalyst, a mixture of cation-exchange resin having a microporous structure and a cation-exchange resin having a macroporous structure.

The required concentration of bisphenol A in the reaction mixture charged to the reaction zone is achieved by appropriately mixing recycled post-crystallization liquors usually containing from 7 to 9 percent by weight of bisphenol A with a part of the reaction mixture from the reaction system or with another technological stream of bisphenol A production, in which the concentration of the product is sufficiently high.

The temperature of the reaction ranges from 60 to 95 degrees C, and the mole ratio of phenol to acetone ranges from 5:1 to 30:1.

It is desirable to carry out the reaction with flow of the reaction mixture from the bottom of a reaction zone up through the cation-exchange resin bed. Conditions are thereby created for better contact or liquid with cation-exchange resin grains in the mass of the bed. This procedure is especially important for high concentrations of the desired product and the reaction by-products in the reaction mixture, in which case there are tendencies to form lumps of cation-exchange resin grains.

It is also preferable to use in the reaction zone, a mixture of cation-exchange resin having a macroporous structure and a cation-exchange resin having a microporous structure in the weight ratio from 0.05:1 to 0.5:1.

Finally, it is desirable to conduct the reaction when the content of ortho-ortho and ortho-para isomers of bisphenol A in the reaction by-products does not exceed 1/4 of the total quantity of reaction by-products.

The method for production of bisphenol A according to the invention increases considerably the selectivity of the reaction of phenol with acetone, reducing to a minimum, the quantity of reaction by-products introduced into the reaction mixture for keeping a stable composition of the technological stream and providing a high quality of the desired product.

In spite of the fact that the present process requires using catalyst quantities in the reaction system several times larger than in other methods, the advantages achieved by the increase of selectivity of the reaction and the reduction of consumption of energy necessary to process the post-reaction mixture because of increased total product content in it more than compensate the costs connected with the construction and the operation of the instant reaction system.

The method according to the invention is illustrated by the examples set forth below:

EXAMPLE I COMPARATIVE

This example illustrates the course of the reaction of phenol with acetone in a reactor operated in the way which has been considered preferable up to now.

The reaction, in the shape of a vertical drum with a diameter of 2400 mm and a height of 10 m, contained Wofatit KPS microporous cation-exchange resin, the height of the cation-exchange resin bed being 7 m.

The flow of the reaction mixture, including substantially anhydrous post-crystallization liquors was directed from the bottom up. The temperature of the reaction mixture at the inflow to the reactor was 75 degrees C, with the flow of the reaction mixture being 6000 kg/h.

The composition of the charge mixture according to chromatographic analysis was:

| COMPONENT | WEIGHT PERCENTAGE |
|---|---|
| bisphenol A | 8.0 |
| by-products | 9.1 including o-o and o-p isomers 3.8 |
| acetone | 6.0 |
| water | 0.2 |
| phenol | rest | color 5 percent r-r in methanol - 70 Hazen units

The composition of the post-reaction mixture leaving the reactor was:

| COMPONENT | WEIGHT PERCENTAGE |
| --- | --- |
| bisphenol A | 17.0 |
| by-products | 10.2 including isomers |
| | 4.3 |
| acetone | 3.5 |
| water | 1.0 |
| phenol | rest |
| color | 125 Hazen units |

The selectivity of the reaction calculated by dividing the quantity of obtained bisphenol A by the sum of obtained by-products and bisphenol A was 89.1 percent. The obtained quantity of bisphenol A was 540 kg.

EXAMPLE II

Through the reactor as described in Example I filled with the same cation-exchange resin bed, there was flowed a reaction mixture obtained by mixing substantially anhydrous post-crystallization liquors with a part of the reaction mixture stream.

The temperature of the reaction mixture at the inflow to the reactor was 75 degrees C, with the flow being 3500 kg/h.

The reaction mixture composition was as follows:

| COMPONENT | WEIGHT PERCENTAGE |
| --- | --- |
| bisphenol A | 16.0 |
| by-products | 15.5 including isomers |
| | 4.4 |
| acetone | 6.0 |
| water | 0.5 |
| phenol | rest |
| color | 100 Hazen units |

The composition of the post reaction mixture leaving the reactor was as follows:

| COMPONENT | WEIGHT PERCENTAGE |
| --- | --- |
| bisphenol A | 24.0 |
| by-products | 16.2 including isomers |
| | 4.8 |
| acetone | 3.8 |
| water | 1.2 |
| phenol | rest |
| color | 125 Hazen units |
| Selectivity of reaction | 92.0 |

The obtained quantity of bisphenol A was 280 kg.

EXAMPLE III

The reactor as described in Example I was filled with the same quantity of ion exchangable resin catalyst, but containing 80 percent of Wofatit KPS microporous cation-exchange resin and 20 percent OK-80 macroporous cation-exchange resin by weight. The height of the cation-exchange resin bed was 7 m.

Through the reactor there was a flow of the reaction mixture from the bottom up in an amount of 3000 kg/h.

The temperature of the reaction mixture at the inflow to the reactor was 75 degrees C, and its composition was as follows:

| COMPONENT | WEIGHT PERCENTAGE |
| --- | --- |
| bisphenol A | 16.5 |
| by-products | 15.2 including isomers |
| | 3.5 |
| acetone | 6.0 |
| water | 0.2 |
| phenol | rest |
| color | 90 Hazen units |

The composition of the reaction mixture leaving the reactor was as follows:

| COMPONENT | WEIGHT PERCENTAGE |
| --- | --- |
| bisphenol A | 25.3 |
| by-products | 15.8 including isomers |
| | 3.7 |
| acetone | 3.8 |
| water | 0.9 |
| phenol | rest |
| color | 100 Hazen units |
| Selectivity of reaction | 93.7 |

The obtained quantity of bisphenol A was 270 kg.

EXAMPLE IV

Through the reactor with the cation-exchange resin charge as in Example III there was dosed a reaction mixture from the bottom up in the quantity of 4000 kg/h.

The temperature of the reaction mixture at the inflow to the reactor was 80 degrees C, and its composition was as follows:

| COMPONENT | WEIGHT PERCENTAGE |
| --- | --- |
| bisphenol A | 18.1 |
| by-products | 20.2 including isomers |
| | 4.5 |
| acetone | 6.0 |
| water | 0.2 |
| phenol | rest |
| color | 100 Hazen units |

The composition of the post-reaction mixture leaving the reactor was as follows:

| COMPONENT | WEIGHT PERCENTAGE |
| --- | --- |
| bisphenol A | 27.1 |
| by-products | 20.7 including isomers |
| | 4.7 |
| acetone | 3.6 |
| water | 1.0 |
| phenol | rest |
| color | 100 Hazen units |
| Selectivity of reaction | 94.7 |

The obtained quantity of bisphenol A was 360 kg.

We claim:

1. A process for the production of bisphenol A from phenol and acetone, which comprises introducing a substantially anhydrous reaction mixture of phenol, acetone, and recycled solution of bisphenol A and reaction by-products in phenol into a reaction zone containing a cation-exchange resin catalyst, said catalyst being a mixture of resin having a macroporous structure and resin having a microporous structure in a ratio of 0.05:to 0.5:1 by weight, the mol ration of phenol to acetone being 5:1 to 30:1, the concentration of bisphenol A being 12 to 20% by weight; maintaining the temperature of the reaction zone between 60 degrees and 95 degrees C; withdrawing the resulting reacted reaction mixture from the reaction zone, the concentration of bisphenol A being 21 to 35% by weight, the amount of reaction by-products being 12 to 24% by weight; and treating such withdrawn reaction mixture to recover bisphenol A product and to provide the recycled solution of bisphenol A and reaction by-products in phenol.

2. A process according to claim 1, in which the concentration of bisphenol A in the reaction mixture introduced into the reaction zone is 15 to 18% by weight.

3. A process according to claim 1, in which the concentration of bisphenol A in the withdrawn reaction mixture is 22 to 28% by weight.

4. A process according to claim 1, in which the amount of reaction by-products in the withdrawn reaction mixture is 16 to 20% by weight.

5. A process according to claim 1, in which the recycled solution of bisphenol A and reaction by-products in phenol includes a portion of the reaction mixture taken from the reaction zone.

6. A process according to claim 1, in which less than ¼ of the reaction by-products contained in the reaction mixture introduced into the reaction zone comprises bisphenol A isomers.

7. A process according to claim 1, in which the reaction zone is vertically arranged, and the reaction mixture is introduced into the lower end of such reaction zone.

* * * * *